(12) United States Patent
Frost

(10) Patent No.: US 7,727,464 B2
(45) Date of Patent: Jun. 1, 2010

(54) PROCESS FOR OPERATING A PACKAGING TRANSPORT SYSTEM

(75) Inventor: Robert Frost, Landshut (DE)

(73) Assignee: PTM Packaging Tools Machinery Pte. Ltd., Singapore (SG)

( * ) Notice: Subject to any disclaimer, the term of this patent is extended or adjusted under 35 U.S.C. 154(b) by 1192 days.

(21) Appl. No.: 10/786,171

(22) Filed: Feb. 26, 2004

(65) Prior Publication Data

US 2004/0228759 A1 Nov. 18, 2004

(30) Foreign Application Priority Data

Feb. 27, 2003 (DE) ................. 103 10 000
Sep. 8, 2003 (DE) ................. 103 41 978

(51) Int. Cl.
*A61L 2/08* (2006.01)
*A61L 2/18* (2006.01)
*A61L 2/24* (2006.01)

(52) U.S. Cl. ............... 422/27; 422/3; 422/28

(58) Field of Classification Search .......... 422/28, 422/3, 27
See application file for complete search history.

(56) References Cited

U.S. PATENT DOCUMENTS 3,117,441 A * 1/1964 Zimmerman ............ 73/37
4,771,630 A * 9/1988 Croce et al. ............ 73/49.3
5,283,033 A * 2/1994 Dodrill ................ 422/21
6,685,895 B1 * 2/2004 Lin .................... 422/297
2002/0054826 A1 * 5/2002 Frost et al. ............ 422/26

FOREIGN PATENT DOCUMENTS

| DE | 10114758 | 9/2002 |
| EP | 0302420 | 2/1989 |
| FR | 2838721 | 10/2003 |
| FR | 2839497 | 11/2003 |
| WO | WO 02/20066 | 3/2002 |
| WO | WO 02/078753 | 10/2002 |

* cited by examiner

*Primary Examiner*—Sean E Conley
*Assistant Examiner*—Kevin C Joyner
(74) *Attorney, Agent, or Firm*—Crowell & Moring LLP

(57) ABSTRACT

A process for operating a packaging transport system in which objects packed in packaging which is bacteria-impermeable but gas-permeable are sterilized, whereafter the packaging, possibly after removal of some packaging parts, is sterilized again on its outer side in a sterilization chamber which acts as a transfer lock, and then guided into a sterile clean room. The objects involved may, in particular, be syringes having injecting needles, which are filled and sealed in a filling device located in the clean room. Sterilization in the sterilization chamber is accomplished by abruptly applying a vapor mix consisting of water steam and hydrogen peroxide vapor as a condensate layer on the outer side of the transport containers, and immediately removing the condensate layer and the uncondensed vapor mix from the sterilization chamber before any significant amount of hydrogen peroxide is deposited inside the transport containers.

25 Claims, 2 Drawing Sheets

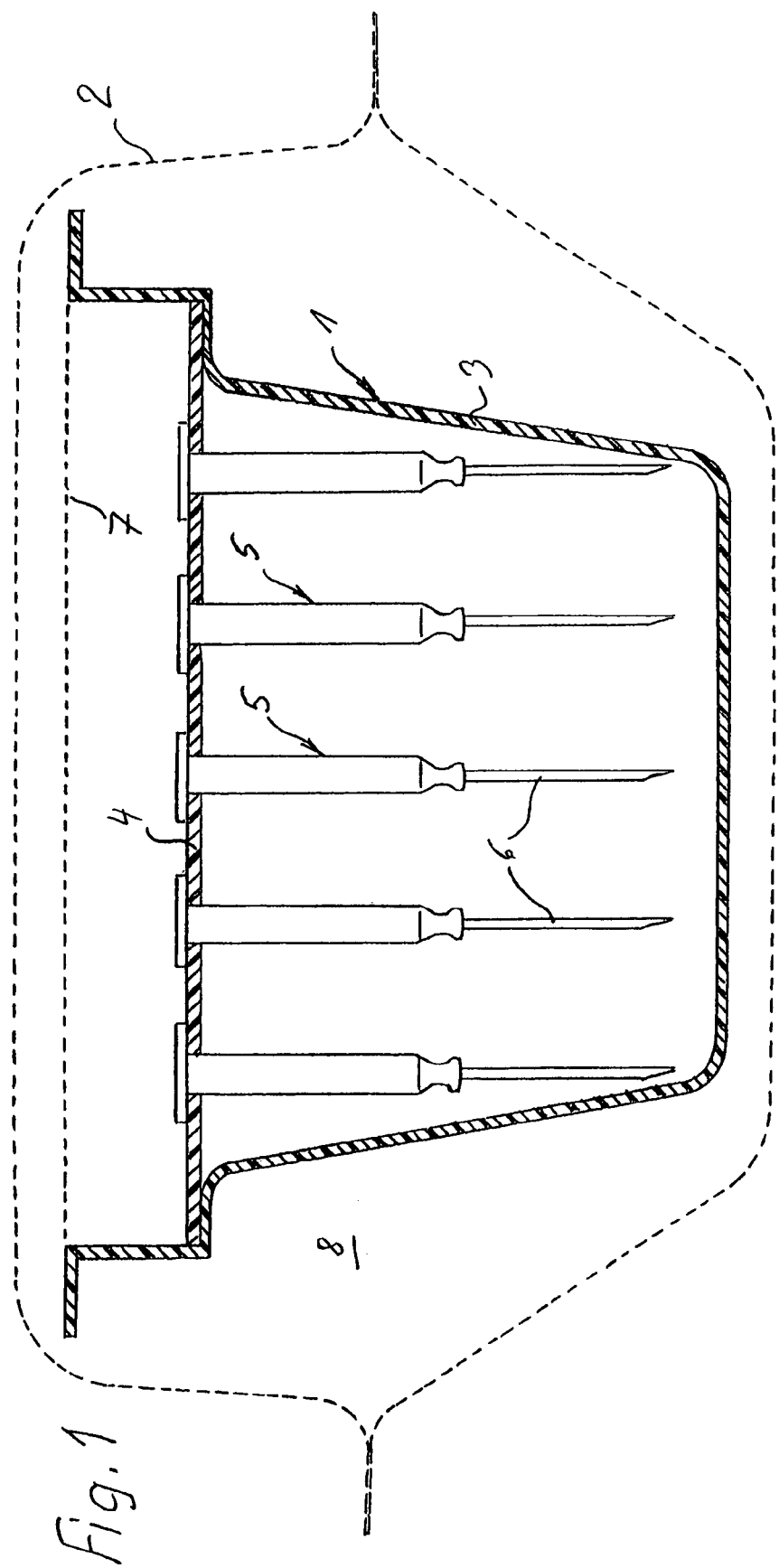

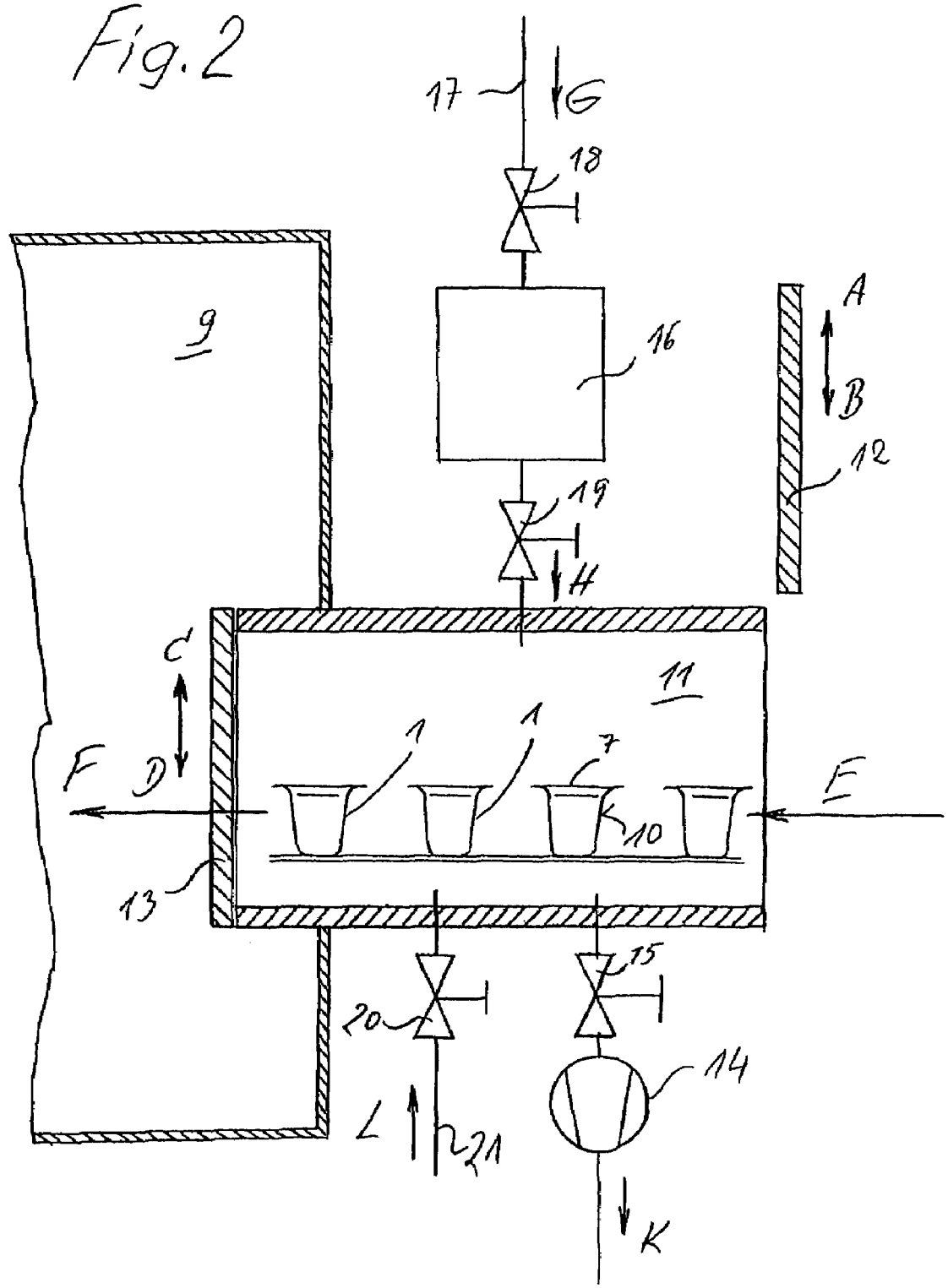

PROCESS FOR OPERATING A PACKAGING TRANSPORT SYSTEM

This application claims the priority of German application Nos. 103 10 000.8, filed Feb. 27, 2003, and 103 41 978.0 filed Sep. 8, 2003 the disclosures of which are expressly incorporated by reference herein.

BACKGROUND AND SUMMARY OF THE INVENTION

The present invention relates to a process for operating a packaging transport system in which contaminated objects are packed in contaminated packaging which is bacteria-impermeable but gas-permeable, said contaminated objects being then sterilized in this state, the packaging then in this state, after the possible removal of some packaging parts, being sterilized again in a transfer lock on its outer side and being guided into a sterile clean room.

The present invention relates in particular to a process for a contamination-free insertion of already sterilized syringes, possibly having injecting needles, into a filling device surrounded by a clean room for filling and sealing of the syringes, in which sterile transport containers (so-called tubs) containing the syringes are provided with a bacteria-impermeable but gas-permeable cover and are sealed in additionally by a similar bacteria-impermeable but gas-permeable packaging, said tubs being first released from the surrounding packaging and thereafter, while still being provided with the cover, are again sterilized on their outer side and guided into the clean room.

A process of the latter mentioned type, for which no previous publication is known to the applicant, is prior art in practice. The above mentioned transport containers or tubs are plastic tubs into which a perforated tray, frequently called a nest, is set. Ready made syringes, which may be provided with adhering needles or needle caps, hang through the holes of the tray. These ready-made syringes are already sterilized and need only to be filled and sealed with a plunger. The plastic tubs are sealed on their upper side by means of a bacteria-impermeable but gas-permeable foil. This consists, as a rule, of polyester and is known under the trademark Tyvek. A foil of this type comprises pores, which are large enough to allow gas molecules to diffuse through, but which are small enough to prevent microorganisms from penetrating the foil.

The tubs are provided with a bag-like packaging, in which also a bacteria-impermeable, but gas-permeable Tyvek strip is integrated. The re-packed tubs are, as a rule, subsequently sterilized with a highly poisonous gas, ethylene oxide. This gas penetrates during sterilization through the surrounding packaging and also through the cover of the plastic tubs into the interior of the tubs and sterilizes hereby all surfaces within the packaging. The ethylene oxide is drawn off again by means of evacuation, and after several days of further removing of poisonous gas in a special store room, the tubs can be sold. It is also known that the tubs can, as an alternative, be sterilized by means of gamma rays.

In order to fill the syringes and to close them by means of a pump plunger, they must be guided into a filling device. The process of filling objects with sensitive, liquid pharmaceuticals always take place under sterile conditions. The filling devices are either installed accordingly in clean rooms or possess their own small clean room, with stands over the filling devices, a so-called isolator.

The difficulty lies in guiding the syringes into the clean room in an absolutely sterile condition without recontaminating them. Clearly, no microorganisms should be hereby permitted to enter the clean room.

In the case of the known process, the packaging, having been disinfected by means of wiping with an alcohol-soaked cloth, is removed outside of the clean room, for example by means of alcohol-disinfected gloves. Even at this point, there is already the danger that particles containing microorganisms will fall from the packaging onto the tub. After the tub has been subsequently inwardly transferred into the clean room, the bacteria-impermeable Tyvek foil is removed from the tub, for example via contact gloves made of hypalon, so that access is gained to the syringes to be filled. Should, however, the Tyvek foil be recontaminated with particles containing microorganisms, these could fall down and land on the syringes when the foil is removed. In order to prevent this, an additional loose sheet of Tyvek lies over the open syringes, which is manually removed just before the nest is inserted into the filler.

In order to minimize the above mentioned risk, it has been the practice for some time that the tub, relieved of the packaging, but still sealed in by the Tyvek cover, is again sterilized, desirable, however, only on the outer side, so that the already sterilized syringes are in no way impaired. This sterilization of the outer side takes place in a type of lock, in which the tub is sterilized by means of high-energy electronic rays (E beams). This one single applicable post-sterilization process has many disadvantages: it is not only costly and technically very complicated, but protection measures against the E beams are necessary. This requires permission for the erection and operation as well as qualified personnel. In addition, aggressive radicals are set free due to the high-energy ionisating beams, which could reach the inner surface of the syringes and which could react with the product in the syringes after filling. The sterilization of the outer side only has remained impracticable.

It is an object of the present invention to construct a technically far simpler, smaller and cheaper lock, which permits a post-sterilization of the outer side of the packaging, in particular of the tubs after being relieved of their packaging and which omits the application of the extremely health-damaging ionisating beams. It should be hereby ensured that the surfaces of the already sterilized syringes which come into contact with the product to be filled in the syringes, are not contaminated with any radicals or otherwise impaired during post-sterilization.

This object has been achieved in accordance with the present invention in that the renewed sterilization of the outer side of the packaging, in particular the transport containers, takes place in an evacuable sterilization chamber which serves as a lock, whereby a vapour mix of water steam and hydrogen peroxide steam is applied abruptly, by means of pre-evacuation of the sterilization chamber, in the form of a condensation layer on the outer side of the packaging or the transport containers, directly thereafter the condensation layer and the vapour mix which has not condensed are removed from the sterilization chamber by means of further evacuation, so that neither the vapour mix nor the condensation layer gets through the packaging or the cover in unadmissible amounts to reach the objects, or in this case, the syringes.

In the process according to the present invention it is initially provided that the sterilization chamber is pre-evacuated using a pump stand, so that the pressure in the sterilization chamber sinks. As soon as pre-evacuation pressure is reached in the sterilization chamber, a vapour mix of water steam and hydrogen peroxide steam flows abruptly into the sterilization chamber without the aid of any carrier gas flow, but driven solely by the difference in pressure between an evaporating apparatus and the pre-evacuated sterilization chamber. As a result of the expansion of the vapour mix, which now not only fills out the volume of the evaporating apparatus, but also that of the much larger sterilization chamber, the vapour mix cools down. The cooling results in a strong oversaturation of the vapour mix, which is why the vapour mix condensates at the moment of entry onto all accessible surfaces within the sterilization chamber. Because of the evaporation enthalpy which is released during condensation, the forming condensate is for a moment heated to such a degree that hydrogen peroxide is dissociated in large amounts, whereby the microorganisms are abruptly destroyed at the moment of condensation of the vapour mix as it expands into the sterilization chamber, before the vapour mix or the condensate layer can penetrate the cover in any inadmissible way.

The speed of the pre-evacuation must be adapted to the flow resistance of the cover of the transport containers. In one variation of the process according to the present invention, this permits the pressure inside the transport containers to be higher than the pressure in the sterilization chamber, at least initially, so that the vapour mix cannot get through the cover into the inside of the transport containers or even as far as to the syringes. The aim is to prevent the condensate formed on the outer side of the cover from being pressed through the gas-permeable foil and into the tubs. The individual parameters, namely the pressure in the evaporator before the flowing-in, the volume ratio between the evaporator and the sterilization chamber, the pre-evacuation pressure as well as the pressure inside the tubs in the moment of the flowing-in of the vapour mix, must, of course, be in the correct ratios to one another.

As in the process described according to the present invention the microorganisms are destroyed instantly in the moment of condensation formation, the removal of the condensation layer from the sterilization chamber can take place, in many cases without waiting for a longer acting time, directly after the flowing-in of the vapour mix. The surfaces covered with a condensate layer located inside the sterilization chamber can be dried by means of simple evacuation of the sterilization chamber down to a pressure below 10 mb, preferably below 1 mb. Because of the difference in pressure which occurs between the inner pressure inside the tubs and the pressure in the sterilization chamber, the air flow out of the tubs is strengthened, so that, expediently as before, no vapour mix can penetrate through the cover into the tubs.

In another variation of the process according to the present invention, use can be made of the fact that the pores of the cover, in size lying in the sub-pm range, prevent even the smallest condensate drops from penetrating. Thanks to the abrupt formation of the condensate, which begins with drops which grow very rapidly and also join together, a kind of sealing effect takes place by means of the condensate being deposited on the pores, so that, expediently, no steam in any great quantities can penetrate through the pores. Even if the sealing effect by the condensate is not in any way complete, it is however good enough to hinder to a great degree the penetration of hydrogen peroxide in the tub for a time span of a few seconds, or at least to slow it down. The sealing effect is technically applicable for a time span of 2 to 4 seconds from the time of the flow-in of the vapour mix; in the case of a less demanding process, for a time span of up to 14 seconds. In the case of a suitable quality of the cover, almost no hydrogen peroxide penetrates into the tubs, even when the pressure in the sterilization chamber during the formation of condensation is higher than the pressure in the inside of the tubs.

The admissible amount of hydrogen peroxide which may be permitted to penetrate through the cover to the inner surfaces of the syringes or to the surfaces of other objects can be considered, within the framework of the present invention, to be a so-called hydrogen peroxide residue, which, for example, measured against the filling volume of the syringes, may not exceed 1.0 ppm (parts per million) and indeed should lie preferably considerably below 0.5 ppm.

From the point of view of a shortening of the duration of the process, both above mentioned variations can be advantageously combined. For practical purposes the process should be so regulated that the inner pressure of the tubs at the start of the flow-in of the vapour mix is significantly higher than the pressure in the sterilization chamber outside of the tubs, but that subsequently the steam pressure of the sterilization chamber which builds up when the vapour mix flows in, is higher than the inner pressure of the tubs, without damaging the condensate for reasons of the sealing effect described above.

A further advantageous embodiment is arrived at when the actual process of subsequent sterilization, namely the depositing of a condensate layer and the subsequent removal of same is repeated at least once. It can hereby in particular be provided that between the end of the removal of the condensate layer of the first sterilization process and the beginning of the depositing of a condensate layer of the subsequent sterilization process the points of support of the tubs on their base is completely changed or displaced, so that any possible areas of the tubs which were covered by the base during the first sterilization process now lie exposed during the second sterilization process. This guarantees that the entire outer-lying surface of the tubs is completely covered at least once by a condensate layer and thus sterilized.

Insofar as the actual process of repeated sterilization is carried out, it is in principal sufficient when the removal of the condensate layer in the previous sterilization process by means of evacuation of the sterilization chamber takes place at a pressure level which lies below the steam pressure of the water at the given temperature of the sterilization chamber, for example up to 70 mb in the case of an exemplary temperature in the sterilization chamber of 40° C. In order to reduce the amount of any hydrogen peroxide which may have penetrated into the tubs, it is however more advantageous to evacuate at below the steam pressure of the applied watery hydrogen peroxide solution at the given temperature in the sterilization chamber, in the case of the named example that is—at a given concentration of the flowing-in vapour mix of 50 percent in weight—at below 42 mb. Even more advantageous, however, is the evacuation of the sterilization chamber under the steam pressure of pure hydrogen peroxide at a given temperature in the sterilization chamber; at a temperature of 40° C. of the sterilization chamber thus below 7 mb.

Other objects, advantages and novel features of the present invention will become apparent from the following detailed description of the invention when considered in conjunction with the accompanying drawings.

BRIEF DESCRIPTION OF THE DRAWINGS

FIG. 1 is a cross section of a covered and packaged transport container comprising syringes, FIG. 2 is a schematic representation of an evacuable sterilization chamber in the form of a lock for sterilizing the outer side of the transport containers which have been released from their packaging.

DETAILED DESCRIPTION OF THE DRAWINGS

The transport container 1 shown in cross section in FIG. 1, a so-called tub, is provided with a packaging 2 denoted by a broken line, which packaging is bacteria-impermeable but gas permeable. The packaging 2 can have several layers, for example, it can consist of two identical pieces of foil, arranged one over the other. The transport container 1 itself is a plastic tub 3, in which a perforated tray 4, a so-called nest, is inserted. A number of syringes 5 are hung from the holes, which syringes already comprise an adhered injecting needle 6, as well as needle sealing caps and needle protecting caps (not shown). These syringes 5 are already sterilized and are yet to be filled and sealed by a plunger. The plastic tub 3 is sealed on its upper side with a bacteria-impermeable but gas-permeable foil-type cover 7. The inside 8 of the packaging 2 is also sterilized during the sterilization of the syringes 5.

In FIG. 2 a schematically shown sterile clean room 9 of a filling device (not shown) is indicated, in which the already sterilized syringes 5 must be re-inserted in a recontamination free state. For this purpose, a sterilization chamber 11, designed as a lock, is provided, in which solely the outer sides 10 of the transport containers 1 are sterilized again after the surrounding packaging 2 has been removed.

At the beginning of a cycle, the sterilization chamber 11 is empty and the loading door 12, movable in the directions of motion A and B, is open. The discharging door 13 is, in contrast, closed, in order to avoid contamination of the clean room 9 via the sterilization chamber 11. The directions of motion of the discharging door 13 are denoted by C and D.

The transport containers 1, relieved of their packaging 2, but still sealed by means of their covers 7, are now transported in feed direction E into the sterilization chamber 11, whereafter the loading door 12 is closed.

At this point, directly before the beginning of pre-evacuation, air at atmospheric pressure is still present inside the transport container 1. The bacteria-impermeable, but gas-permeable cover 7 demonstrates a considerable flow resistance, which signifies that the air, in evacuated surroundings, can only flow slowly outwards through the cover 7. Pre-evacuation now takes place via a pump stand 14 so rapidly that the pressure in the sterilization chamber 11 initially falls much quicker than the pressure inside the transport containers 1.

As soon as the desired pre-evacuation pressure is reached in the sterilization chamber 11, the pumping-off valve 15 is closed off towards the pump stand 14 and directly thereafter, almost simultaneously, a steam valve 19 to an evaporator 16 is opened. A watery solution comprising a suitable concentration of hydrogen peroxide is fed via a conduit 17 and via a feed valve 18 in feed direction G to the evaporator 16, thereafter an overheated vapour mix of water steam and hydrogen peroxide steam is generated in the evaporator. After the steam valve 19 has been opened, the vapour mix can flow in in steam feed direction H into the sterilization chamber 11 without the aid of carrier gas, but driven solely by means of the difference in pressure between the evaporator 16 and the pre-evacuated sterilization chamber 11. Thereafter, sterilization of the outer sides 10 only of the individual transport containers 1 takes place as described above. At this stage of the process, the pressure in the inside of the transport containers 1 is lower than in the sterilization chamber 11 outside of the transport containers 1.

As the destruction of the microorganisms takes place directly in the moment of the formation of condensation, the removal of the condensation layer from the sterilization chamber 11 can take place immediately after the vapour mix has stopped flowing in and the steam valve 19 has been closed, without a waiting period for the condensation to act. Only the pumping-off valve 15 is opened again for this purpose. This causes the pressure in the sterilization chamber 11 to be lowered very quickly, namely so low that this pressure is then below the steam pressures of both components of the condensation layer, whereby these evaporate and are sucked out of the sterilization chamber 11 by means of the pump stand 14. After the drying phase has been completed, the pumping-off valve 15 is closed and a flood valve 20 is opened, so that sterile flood gas, as a rule sterile air, can flow in via a conduit 21 in feed direction L into the sterilization chamber 11, until the pressure in the sterilization chamber 11 corresponds to the pressure in the sterile clean room 9. In order to discharge, the discharging door 13 is opened, whereby the transport containers 1, sterilized for a second time on their outer sides 10 are guided in delivery direction F into the sterile clean room 9. The loading door 12 remains closed until the discharging door 13 is fully closed again after the transport containers 1 have been removed and the discharging door 13 has sealed the clean room 9. When the loading door 12 is re-opened, the start of the cycle has again been reached.

As can be seen from the course of the process, particular attention is paid to the phase of the pre-evacuation. By means of careful controlling of the pressure ratios in the sterilization chamber 11, it should be ensured that the occurring differences between the pressures outside and inside of the transport containers 1 do not become so large that the securing devices of the covers 7 are damaged. The foil-like covers 7 can, due to the occurring differences in pressure, become deformed, which, however, is not detrimental to the covers themselves.

Should the cover 7 partly come loose from the plastic tub 3, for example due to a faulty securing device of the cover 7 on the plastic tub 3, the result would be an unacceptably high hydrogen peroxide residue on the objects located in the transport containers 1, for example the syringes 5, as when the vapour mix flows into the sterilization chamber 11, it can get to the objects directly. Because the pressure in the transport containers 1 during pre-evacuation is initially significantly higher than the pressure in the sterilization chamber 11 outside of the transport containers 1, there is a short blast of pressure should the cover 7 be ripped open, which blast is registered by a pressure indicator. Such a blast of pressure can be processed by the control unit of the installation so that a warning is given to the effect that the relevant transport container 1 or possibly the entire load of the sterilization chamber 11 is removed from the cycle.

Should a transport container 1 or its cover 7 be already damaged when it enters the sterilization chamber 11, before the second sterilization takes place, this will also be registered while the process is in progress. This is a great advantage of the invention over prior art.

As long as the pressure in the inside of the transport containers 1 lies above the pressure of the sterilization chamber 11 during pre-evacuation or during further evacuation for removing the condensate layer, the flexible cover 7 can curve outwards. If a cover 7 or a transport container 1 is damaged in such a way that the gas can escape through this opening more rapidly that would be the case owing to the flow resistance of the cover 7, the cover 7 then curves only minimally outwards or not at all.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for operating a packaging transport system, comprising the steps of:
   sterilizing objects packed in at least one layer of packaging which is bacteria-impermeable and gas-permeable;
   placing the sterilized objects packed in at least one layer of the at least one layer of packaging into an evacuable sterilization chamber in the form of a transfer lock;
   pre-evacuating the sterilization chamber at a speed, wherein the speed of the pre-evacuation is adapted to the flow resistance of the gas-permeable packaging to ensure a gas pressure within the packaging remains above a pressure in the sterilization chamber during the pre-evacuation;
   applying abruptly a vapor mix consisting of water steam and hydrogen peroxide steam as a condensate layer onto the outer side of the packaging;
   re-evacuating the sterilization chamber to remove the condensate layer and the uncondensed vapor mix before either the vapor mix or the condensate layer penetrates through the packaging to the objects at an inadmissible level; and
   transferring the sterilized objects and packaging into a sterile clean room.

2. A process according to claim 1, wherein a pressure difference between a pressure of the vapor mix and a pressure in the evacuated sterilization chamber forces the vapor mix to be fed into the sterilization chamber without the use of carrier gas.

3. A process according to claim 1, wherein the condensate layer is removed from the sterilization chamber immediately after the vapor mix has been fed into the sterilization chamber.

4. A process according to claim 1, wherein the condensate layer is applied before an inner pressure of the packaging has reached a pressure of the sterilization chamber.

5. A process according to claim 1, wherein the level of hydrogen peroxide residue does not exceed 0.5 ppm.

6. A process according to claim 1, wherein a time span of 14 seconds is provided from the beginning of the flowing in of the vapour mix to the beginning of the re-evacuation.

7. A process according to claim 6, wherein the time span amounts to a maximum of 4 seconds.

8. A process according to claim 6, wherein the time span amounts to a maximum of 2 seconds.

9. A process according to claim 1, wherein the pre-evacuation, vapor mix application and re-evacuation steps are repeated at least once.

10. A process according to claim 1, wherein a packaging leakage is detected by analysis of sterilization chamber pressure.

11. A process according to claim 10, wherein packaging leakage is detected during at least one of the pre-evacuation step and the re-evacuation step.

12. A process according to claim 1, wherein a package leakage occurring before the package is guided into the sterilization chamber is detected by monitoring the curvature of the package.

13. A process according to claim 12, wherein a package leakage is detected by monitoring the curvature of the package during at least one of the pre-evacuation step and the re-evacuation step.

14. A process according to claim 1,
   wherein the packaging sterilized on the outer side is a transport container containing already sterilized syringes with a bacteria-impermeable and gas-permeable cover and a bacteria-impermeable and gas permeable additional packaging;
   wherein the transport container is released from the sealed bacteria-impermeable and gas permeable additional packaging before placing the transport container in the sterilization chamber;
   wherein the speed of the pre-evacuation is adapted to the flow resistance of the gas-permeable cover of the transport container; and
   wherein the sterilized transport container is guided into the clean room for syringe filling in the filling operation.

15. A process according to claim 14, wherein a pressure difference between a pressure of the vapor mix and a pressure in the evacuated sterilization chamber forces the vapor mix to be fed into the sterilization chamber without the use of carrier gas.

16. A process according to claim 14, wherein the condensate layer is removed from the sterilization chamber immediately after the vapor mix has been fed into the sterilization chamber.

17. A process according to claim 14, wherein the condensate layer is applied before an inner pressure of the packaging has reached a pressure of the sterilization chamber.

18. A process according to claim 14, wherein removal of the additional packaging is not performed if the porosity of the transport container is above a predetermined value.

19. A process according to claim 18, wherein supporting surfaces of the transport container adapted for use with a holding device or a transport device, and the support surfaces are altered before the pre-evacuation, vapor mix application and re-evacuation steps are repeated.

20. A process according to claim 18, wherein during a repeat of the pre-evacuation, vapor mix application and re-evacuation steps, the removal of the condensate layer takes place by evacuation of the sterilization chamber to a pressure level below at least one of a steam pressure of water, a steam pressure of water and hydrogen peroxide solution, and a steam pressure of pure hydrogen peroxide, corresponding to a temperature in the sterilization chamber during sterilization.

21. A process according to claim 14, wherein the pre-evacuation, vapor mix application and re-evacuation steps are repeated at least once.

22. A process according to claim 14, wherein transport container leakage is detected by analysis of sterilization chamber pressure.

23. A process according to claim 22, wherein a package leakage is detected during at least one of the pre-evacuation step and the re-evacuation step.

24. A process according to claim 14, wherein a package leakage occurring before the package is guided into the sterilization chamber is detected by monitoring the curvature of the package.

25. A process according to claim 24, wherein a package leakage is detected by monitoring the curvature of the package during at least one of the pre-evacuation step and the re-evacuation step.

* * * * *